(12) United States Patent
Naya

(10) Patent No.: US 7,057,731 B2
(45) Date of Patent: Jun. 6, 2006

(54) MEASURING METHOD AND APPARATUS USING ATTENUATED TOTAL REFLECTION

(75) Inventor: Masayuki Naya, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 10/669,651

(22) Filed: Sep. 25, 2003

(65) Prior Publication Data

US 2004/0061860 A1    Apr. 1, 2004

(30) Foreign Application Priority Data

Sep. 27, 2002    (JP)    ............................. 2002-284122

(51) Int. Cl.
*G01N 21/55* (2006.01)
(52) U.S. Cl. ..................................... 356/445
(58) Field of Classification Search ................ 356/445, 356/128, 134–136, 317, 318
See application file for complete search history.

(56) References Cited

U.S. PATENT DOCUMENTS

| | | | | |
|---|---|---|---|---|
| 4,253,765 A | * | 3/1981 | Kato et al. | .................. 356/328 |
| 5,880,833 A | * | 3/1999 | Iwasaki | ........................ 356/328 |
| 5,973,780 A | * | 10/1999 | Tsuboi et al. | ................ 356/328 |
| 2002/0094528 A1 | * | 7/2002 | Salafsky | ........................ 435/6 |
| 2003/0048452 A1 | * | 3/2003 | Johansen | ..................... 356/445 |
| 2003/0113231 A1 | * | 6/2003 | Karube et al. | ............ 422/82.05 |

FOREIGN PATENT DOCUMENTS

| | | |
|---|---|---|
| JP | 6-167443 A | 6/1994 |
| WO | WO 200190728 A1 * | 11/2001 |

OTHER PUBLICATIONS

Jiri Homola, et al./Surface Plasmon Resonance Sensors Based on Diffraction Gratings and Prism Couplers: Sensitivity Comparison/Sensors and Actuators B 54 (1999) 16-24.

\* cited by examiner

*Primary Examiner*—Layla G. Lauchman
*Assistant Examiner*—Gordon J. Stock, Jr.
(74) *Attorney, Agent, or Firm*—Sughrue Mion, PLLC

(57) ABSTRACT

A small-sized measuring apparatus having a stray light suppressing capability for detecting the distribution of optical intensities on the cross section of a light beam having a predetermined wavelength contained in a light beam reflected from a measuring surface by entering a collimated light beam having a large cross sectional area into the measuring surface. A collimated light beam having a sufficient cross sectional area is entered into the interface between a dielectric block and a thin metal film formed on the dielectric block at an angle that satisfies the conditions of total reflection. A light beam having a predetermined wavelength is selected from the light beam totally reflected at the interface to detect the distribution of optical intensities for the selected light beam by the wavelength selecting section capable of eliminating stray light.

39 Claims, 4 Drawing Sheets

MEASURING METHOD AND APPARATUS USING ATTENUATED TOTAL REFLECTION

BACKGROUND OF THE INVENTION

1. Field of the Invention

The present invention relates to a measuring method and apparatus using attenuated total reflection, such as, for example, a surface plasmon resonance measuring apparatus in which a particular substance in a sample is analyzed by attenuated total reflection induced by the excitation of surface plasmons. More specifically, the present invention relates to a measuring method and apparatus that uses attenuated total reflection, in which the state of attenuated total reflection at an area of measurement having a two-dimensional area is detected by a collimated light beam of a certain wavelength selected from a plurality of wavelengths.

2. Description of the Related Art

In a metal, free electrons oscillate as a group and a compressional wave called a plasma wave is generated. The quantized compressional waves generated on the surface of a metal are known as surface plasmons.

Various surface plasmon resonance measuring apparatus have been proposed for analyzing the properties of a sample by applying the phenomenon that the surface plasmons are excited by a light wave. Among these measuring apparatus, the one that uses a system called Kretschmann configuration is particularly well-known as described, for example, in Japanese Unexamined Patent Publication No. 6(1994)-167443.

Basically, the surface plasmon resonance measuring apparatus that uses the system described above comprises, for example, a dielectric block shaped like a prism; a metal film formed on one of the surfaces of the dielectric block and brought into contact with a sample; a light source for generating a light beam; an optical system for entering the light beam into the dielectric block at various incident angles including an angle that satisfies the conditions of total reflection and surface plasmon resonance at the interface between the dielectric block and the metal film; and a optical detecting means for detecting the state of surface plasmon resonance by measuring the intensity of the light beam totally reflected at the interface.

When a light beam enters the metal film of a surface plasmon resonance measuring apparatus configured in the aforementioned manner at a certain incident angle $\theta_{sp}$ which is not smaller than the total reflection angle, an evanescent wave having a distributed electric field is generated in the sample in contact with the metal film, and thereby surface plasmons are excited at the interface between the metal film and the sample. When the wave number matching is achieved, in which the wave-number vector of the evanescent light matches the wave-number vector of the surface plasmons, the evanescent light and the surface plasmons go into the state of resonance, and the intensity of the light totally reflected at the interface between the dielectric block and the metal film drops sharply, because the light energy is transferred to the surface plasmons. This drop in the intensity of light is generally detected as a dark line by the optical detecting means described above. Thus, the wave number of the surface plasmon is determined by the attenuated total reflection angle $\theta_{sp}$, which is the incident angle that causes the attenuated total reflection.

In such a type of surface plasmon resonance measuring apparatus described above, the resonant wave number is measured by sweeping a range of incident angles of a single wavelength, or by entering a light beam at various incident angles. On the other hand, it may also be measured by sweeping a range of wavelengths with a fixed incident angle as described, for example, in "Surface plasmon resonance sensors based on diffraction grating and prism couplers: sensitivity comparison"; Sensors and Actuators B 54 (1999), P16 to 24.

As for the surface plasmon resonance measuring apparatus that employs the swept wavelength method, an apparatus comprising a light source for generating a light beam having a plurality of wavelengths; a wavelength selecting section for sweeping a range of wavelengths by sequentially selecting a desired light beam of a single wavelength from the light beam, an optical system for entering the selected light beam of the single wavelength into the dielectric block at an angle that satisfies the conditions of total reflection at the interface between the dielectric block and the metal film, and a optical detecting means for measuring the intensity of the light beam totally reflected at the interface is known as described, for example, in "Porous Gold in Surface Plasmon Resonance Measurement"; EUROSENSORS X111, 1999, P585 to 588.

The measuring apparatus described above detects the wave number of the surface plasmon by repeating the measurement through repeated wavelength sweeping with a fixed incident angle, and by detecting the attenuated total reflection wavelength $\lambda_{SP}$ which is the wavelength that causes the attenuated total reflection. The resonance described above occurs only when the incident light beam is in a p-polarized mode. Accordingly, arrangements need to be made in advance so that the light beam enters in the p-polarized mode.

When the resonant wave number, that is, the wave number of the surface plasmon is detected, the dielectric constant of the sample maybe obtained. More specifically, the following relationship may be obtained, assuming that Ksp is the wave number of surface plasmons, $\omega$ the angular frequency of the surface plasmon, c the speed of light in vacuum, $\in_m$ the dielectric constant of the metal, and $\in_s$ the dielectric constant of the sample.

$$Ksp(\omega) = \frac{\omega}{c}\sqrt{\frac{\varepsilon_m(\omega)\varepsilon_s}{\varepsilon_m(\omega)+\varepsilon_s}}$$

When the dielectric constant $\in_s$ is determined, the refractive index of the sample may be obtained based on a predefined calibration curve and the like. That is, by determining the attenuated total reflection angle $\theta_{sp}$, or the attenuated total reflection wavelength $\lambda_{SP}$ that causes the attenuated total reflection described above, the refractive index of the sample or characteristics related to the refractive index of the sample may be obtained.

A leaky mode measuring apparatus using, for example, a dielectric cladding layer is also known as a similar sensor that uses attenuated total reflection as described, for example, in "BUNKOH KENKYU"; Vol. 47, No.1 (1998) P 21 to 23, and P26 to 27. Basically, the leaky mode measuring apparatus comprises, for example, a dielectric block shaped like a prism; a cladding layer formed on one of the surfaces of the dielectric block; an optical waveguide layer formed on the cladding layer and brought into contact with the sample; a light source for generating a light beam; an optical system for entering the light beam into the dielectric block at various angles to satisfy the conditions of total reflection at the interface between the dielectric block and the cladding layer, and to cause attenuated total reflection by the excitation of a waveguide mode in the optical waveguide layer; and a optical detecting means for detecting the state of excitation of the waveguide mode or attenuated total reflection by measuring the intensity of the light beam totally reflected at the interface.

When a light beam is incident on the cladding layer through the dielectric block of a leaky mode measuring apparatus configured in the aforementioned manner at a certain incident angle not smaller than the total reflection angle, a certain light component of the light beam having particular wave number and incident angle passes through the cladding layer, and propagates along the optical waveguide layer in a waveguide mode. When the waveguide mode is excited in this manner, attenuated total reflection occurs, in which the intensity of the light totally reflected at the interface described above drops sharply, because most of the incident light is contained in the optical waveguide layer. The wave number of the guided light is dependent on the refractive index of the sample placed on the optical waveguide layer, so that the refractive index of the sample and other characteristics related thereto may be analyzed by determining the attenuated total reflection angle $\theta_{SP}$ that causes the attenuated total reflection described above. The refractive index or the characteristics related to the refractive index of the sample may also be analyzed by detecting the attenuated total reflection wavelength $\lambda_{SP}$ by sweeping a range of wavelengths with a fixed incident angle as in the surface plasmon resonance measuring apparatus described above.

In the analysis of the properties of a sample with the surface plasmon resonance measuring apparatus, or leaky mode measuring apparatus, it may often be required to measure the properties of a plurality of samples under the same measuring conditions, or to obtain information on two-dimensional properties of a sample, thus the application of these apparatuses to these fields has been contemplated. Taking the two-dimensional property measurement for a sample using the surface plasmon resonance measuring apparatus, as an example, when a collimated light beam having a predetermined wavelength enters into a region of the interface having a two-dimensional area at a predetermined incident angle, the light component totally reflected from the section of the region where the refractive index of the sample is such that the attenuated total reflection is induced by the predetermined incident angle and wavelength is detected as a dark spot. Thus, the characteristics of the sample related to the two-dimensional distribution of the refractive indices of the sample along the interface may be measured by using a collimated light beam having a sizable cross section, and containing a plurality of wavelengths; selecting a desired collimated light beam of a single wavelength therefrom; entering the selected light beam into the interface between the dielectric block and the metal film; and detecting the distribution of the optical intensities on the cross section of the collimated light beam totally reflected at the interface as described, for example, in "Development of a Two-Dimensional Evaluation Method for Thin Layers Using Surface Plasmon Resonance"; Chemistry Letters 2001, P1312 to 1313.

The above description may also be applied to the leaky mode measuring apparatus except that the attenuated total reflection is induced by the excitation of the waveguide mode in the optical waveguide layer, instead of by surface plasmon resonance, so that the two-dimensional properties of a sample described above may also be obtained in the similar manner by using the leaky mode measuring apparatus.

The measuring apparatus described in the document entitled "Development of a Two-Dimensional Evaluation Method for Thin Layers Using Surface Plasmon Resonance" described above enters a collimated light beam having a desired single wavelength selected from a collimated light beam having a plurality of wavelengths into the interface between the dielectric block and the metal film, and detects the distribution of the optical intensities on the cross section of the reflected light beam by a optical detecting means, so that a wavelength selection filter needs to be placed in the optical path in the vicinity of the optical detecting means for passing only the light components having wavelengths close to the wavelength of the collimated light beam reflected at the interface in order to block stray light, such as ambient light. Further, when sweeping a range of wavelengths of the collimated light beam, the range of the wavelengths passing through the wavelength selection filter must also be swept over. Consequently, the wavelength selection filter becomes complicated and large, contributing to larger size and increased cost of the measuring apparatus.

SUMMARY OF THE INVENTION

The present invention has been developed in recognition of the circumstance described above, and it is an object of the present invention to provide an inexpensive and small measuring apparatus and method using attenuated total reflection.

The measuring method using attenuated total reflection according to the present invention comprises the steps of:

entering a collimated light beam containing a plurality of wavelengths, and having a sizable cross sectional area, through a dielectric block of a measuring unit comprising a thin film layer formed on one of the surfaces of said dielectric block, and a sample holding structure for holding a sample provided on said thin film layer, into the interface between said dielectric block and said thin film layer at an angle that satisfies the conditions of attenuated total reflection at said interface;

selecting a collimated light beam having a predetermined wavelength from the collimated light beam totally reflected from said interface; and measuring the distribution of optical intensities on the cross section of said selected light beam.

The "collimated light beam" is not limited to a perfectly collimated light beam, but includes a converging or diverging light beam as long as it allows the measurement of the state of attenuated total reflection. Preferably, the dielectric block described above is transparent to the plurality of wavelengths described above, which will be also applied hereinafter.

The measuring method using attenuated total reflection described above may be a measuring method that selects a plurality of light beams of different wavelength simultaneously at the step of selecting a collimated light beam having a predetermined wavelength, and detects the respective distributions of optical intensities on the cross sections of the plurality of collimated light beams of different wavelength.

The measuring apparatus using attenuated total reflection according to the present invention comprises:

a measuring unit comprising a thin film layer formed on one of the surfaces of a dielectric block, and a sample holding structure for holding a sample provided on said thin film layer;

an illuminating means for entering a light beam containing a plurality of wavelengths, and having a sizable cross sectional area, which is generated and emitted from a light source, into the interface between said dielectric block and said thin film layer, through said dielectric block, at an angle that satisfies the conditions of total reflection at said interface;

a wavelength selecting means disposed in the optical path of the collimated light beam totally reflected from said interface, and adapted to select a collimated light beam having a predetermined wavelength from said collimated light beam containing said plurality of wavelengths; and a two-dimensional optical detecting means for detecting the distribution of optical intensities on the cross section of said collimated light beam selected by said wavelength selecting means.

If the wavelength selecting means is a wavelength selecting means adapted to select a plurality of collimated light beams of different wavelength simultaneously, it is preferable that the two-dimensional optical detecting means is a two-dimensional optical detecting means adapted to detect the respective distributions of optical intensities on the cross sections of the plurality of collimated light beams of different wavelength.

The measuring apparatus described above may be a measuring apparatus having a dispersion suppressing structure for suppressing dispersion of the collimated light beam at the dielectric block.

A dielectric block formed such that the optical entrance surface thereof becomes perpendicular to the optical axis of the collimated light beam described above may constitute the dispersion suppressing structure.

Further, the measuring apparatus described above may be a measuring apparatus having a dispersion compensating means for compensating for dispersion of the collimated light beam at the dielectric block.

A sensing material that interacts with a specific component of a sample may be placed on the thin film layer described above. In this case, the same kind of sensing material or a plurality of sensing materials of different kinds may be placed on the different areas of the thin film layer. When a plurality of sensing materials is placed on the different areas of the thin film layer, the "sizable cross sectional area" described above means a cross sectional area capable of illuminating the light beam substantially across the plurality of sensing materials simultaneously.

The dielectric block described above may be a dielectric block comprising a first part having an optical entrance and outgoing surfaces for the collimated light beam, and a second part formed independently of the first part as a separate body having a surface on which the thin film layer is formed, which is connected to the first part through a refractive index matching means. That is, the second part is replaceable with respect to the first part.

The measuring unit described above may be a dielectric block comprising a dielectric block, thin film layer, and sample holding structure integrated into a single unit.

The wavelength selecting means described above may be a wavelength selecting means comprising a separating means for separating the collimated light beam into spectral components; a selecting means for converging a part of the spectral components to pass through a slit, and thereafter transforming the converged spectral component into a collimated light beam; and a sweeping means for changing the relative angle between the separating means and selecting means.

The separating means described above may be a diffraction grating, or prism.

The measuring method and apparatus according to the present invention enter a collimated light beam containing a plurality of wavelengths, and having a sizable cross sectional area, through a dielectric block of a measuring unit comprising a thin film layer formed on one of the surfaces of the dielectric block and a sample holding structure for holding a sample provided on the thin film layer, into the interface between the dielectric block and the thin film layer at an angle that satisfies the conditions of attenuated total reflection at the interface; select a collimated light beam having a predetermined wavelength from the collimated light beam totally reflected at the interface; and measure the distribution of optical intensities on the cross section of the selected collimated light beam, so that the stray light may be blocked in the step of selecting a predetermined wavelength, and the wavelength selection filter employed in the conventional measuring method and apparatus using attenuated total reflection may be eliminated; thereby reduced size and cost for the measuring apparatus may be realized.

Further, if a plurality of collimated light beams of different wavelengths is selected simultaneously in the step of selecting a collimated light beam having a predetermined wavelength, and the respective distributions of the optical intensities on the cross sections of the plurality of light beams are detected, the measuring efficiency may be enhanced. In addition, comparisons among the states of attenuated total reflection for different wavelengths may be made.

If the dispersion suppressing structure for suppressing the dispersion of the collimated light beam at the dielectric block is provided, the dispersion of the collimated light beam at the dielectric block is suppressed; thereby the accuracy of the measurement may be improved. Further, if the dielectric block formed in such a manner that the optical entrance surface thereof is perpendicular to the optical axis of the collimated light beam serves as the dispersion suppressing structure, a separate dispersion suppressing structure is unnecessary.

Further, if a dispersion compensating means for compensating for the dispersion of the collimated light beam at the dielectric block is provided, the dispersion of the collimated light beam at the dielectric block may be compensated for; thereby the accuracy of the measurement may be improved.

If the sample described above is a liquid sample, and a sensing material that interacts with a specific component of the sample is placed on the thin film layer described above, the interaction between the sensing material and the specific component of the sample, if any, may be detected. Further, if a plurality of sensing materials is placed on the different areas of the thin film layer, different kinds of particular substances in the sample that interact respectively with the plurality of sensing materials are detected simultaneously, thereby the measuring efficiency may be enhanced.

If the dielectric block described above comprises a first part having a optical entrance and outgoing surfaces for the collimated light beam, and a second part formed independently of the first part as a separate body having a surface, on which the thin film layer is formed, which is connected to the first part through a refractive index matching means, the second part is replaceable with respect to the first part.

This means that the measurement may be conducted sequentially by using a number of second parts with the single first part, so that the measuring cost may be reduced.

Further, if the measuring unit described above is a measuring unit comprising a dielectric block, thin film layer, and sample holding structure integrated into a single unit, measurement with a number of measuring units may be implemented by changing the unit one after the other; thereby the measuring efficiency may be enhanced.

DESCRIPTION OF THE PREFERRED EMBODIMENTS

Figure 1:
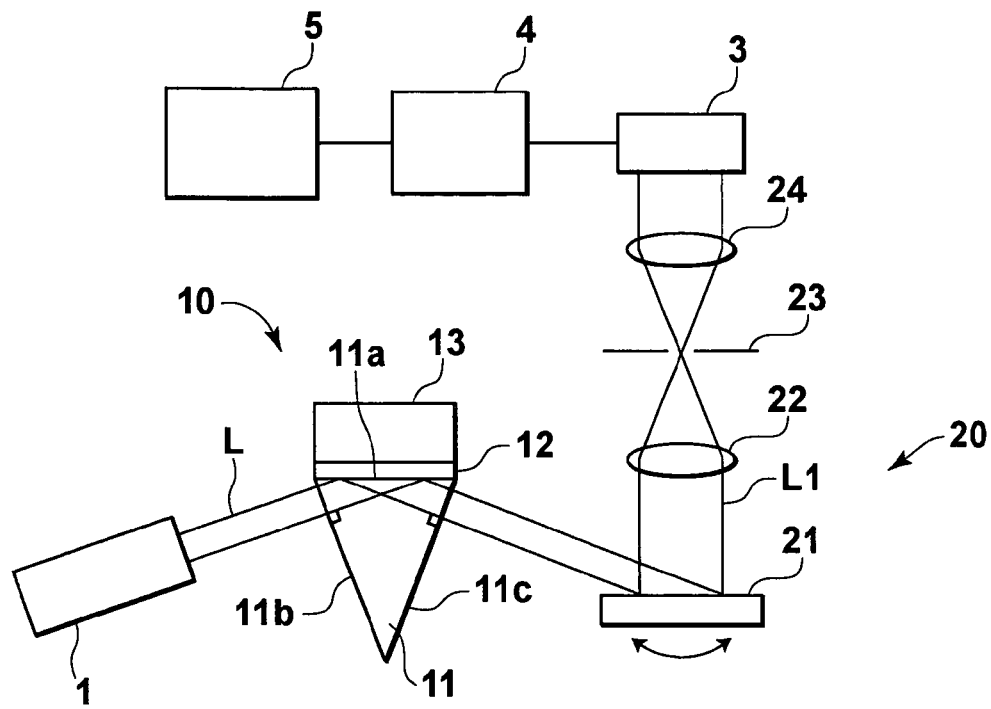
FIG. 1 is a side view of a surface plasmon resonance measuring apparatus according to a first embodiment of the present invention.

Hereinafter, the preferred embodiments of the present invention will be described in detail with reference to the accompanying drawings. FIG. 1 shows a measuring apparatus according to a first embodiment of the present invention, illustrating a schematic side view thereof.

The measuring apparatus according to the first embodiment is constructed as a surface plasmon resonance apparatus described above. In this surface plasmon resonance measuring apparatus, a measuring unit 10 has a dielectric prism 11 made of a transparent resin, e.g., PMMA, or an optical glass, e.g., BK7, shaped like, for example, a triangular column, and a thin metal film 12 made of, for example, gold, silver, copper, or aluminum formed on the upper surface of the dielectric prism 11 (a surface 11a in FIG. 1), and a sample 13 for analysis is placed on the thin metal film 12. The dielectric block 11 and the thin metal film 12 disposed in the manner as illustrated in FIG. 1 serves as a sample holding structure of the present invention.

The surface plasmon resonance measuring apparatus shown in FIG. 1 comprises the measuring unit 10 described above; a light source 1 for emitting a light beam L of a collimated white light beam having a sizable cross sectional area, and containing a plurality of wavelengths; a wavelength selecting section 20 for selecting a light beam L1 having a desired wavelength from the light beam L entered into the dielectric prism 11 from a surface 11b, not the surface carrying the thin metal film 12, reflected at the interface between the dielectric prism 11 and the thin metal film 12, and exited from another surface 11c of the prism 11; a CCD 3 for picking up the image of the distribution of optical intensities for the light beam L1 selected by the wavelength selecting section 20 as a two-dimensional image; a signal processing section 4 for processing the image signal outputted from the CCD 3; and a display section 5 for displaying the image signal outputted from the signal processing section 4 as an image.

The dielectric prism 11 serves as a dielectric block of the present invention, and is shaped in such a manner that the light beam L enters on the surface 11b of the prism 11 at an angle substantially perpendicular thereto, and the light beam L totally reflected at the interface 11a exits from the surface 11c of the prism 11 at an angle substantially perpendicular thereto.

The wavelength selecting section 20 comprises a swept-wavelength diffraction grating 21 for separating the light beam L into spectral components; and three other optical components disposed linearly between the diffraction grating 21 and a CCD 3, namely a converging lens 22, slit 23, and collimating lens 24. The slit 23 is disposed in the vicinity of the focal point of the converging lens 22 to block light other than the light reflected from the diffraction grating 21 at a predetermined angle. This allows that only the light beam L1 having a wavelength within a desired band of wavelengths is selected, and the image of the distribution of optical intensities for the selected light beam L1 is picked up by the CCD 3.

A motor (not shown) is connected to the diffraction grating 21, and the diffraction grating 21 is rotated by the motor on an axis perpendicular to the surface formed by the incident light beam L and a reflected light beam reflected from the diffraction grating as the rotational axis to vary the incident angle of the light beam L at the diffraction grating 21, which leads to the change in the wavelength of the light beam L1 entering into the converging lens 22. In this embodiment, the angle of the diffraction grating 21 is adjusted so that the light beam L1 having a wavelength $\lambda 1$ may enter into the converging lens 22.

Hereinafter, the operation of the surface plasmon resonance measuring apparatus of the above configuration will be described. The light beam L emitted from the light source 1 enters into the surface 11b of the prism 11 at an angle substantially perpendicular thereto, passes through the prism 11, and is incident on the interface between the prism 11 and the thin metal film 12. The light beam L is a collimated white light beam having a sizable cross sectional area, and containing a plurality of wavelengths. The incident angle $\theta$ of the light beam L at the interface 11a is adjusted in such a manner that the conditions of total reflection at the interface 11a are satisfied, and attenuated total reflection due to surface plasmon resonance may be detected by the predetermined wavelength $\lambda 1$ if a particular substance in a sample is present on the thin metal film 12.

The light beam L needs to be incident on the interface 11a in a p-polarized mode to excite the surface plasmon resonance as described above, which may be effected by pre-adjusting the light source 1 to emit such light beam L, or by controlling the direction of the polarization of the light beam L with a wavelength plate or a polarization plate.

The light beam L incident on the interface 11a is totally reflected at the interface, and the light beam L totally reflected at the interface exits from the surface 11c of the dielectric prism 11, and enters into the diffraction grating 21 to be separated. Only the light beam L1 having a wavelength $\lambda 1$ is selected through the converging lens 22, slit 23, and collimating lens 24, and enters into the CCD 3. In the CCD 3, the image of the distribution of optical intensities for the light beam L1 is picked up as a two-dimensional image, which is processed in the signal processing section, and displayed on the display section 5.

In this case, the distribution of optical intensities for the light beam L1 having a desired wavelength $\lambda 1$ may be obtained by pre-adjusting the angle of the diffraction grating 21, so that a desired wavelength $\lambda 1$ is selected, or the distribution of optical intensities for the light beam L1 containing a plurality of wavelengths may be obtained sequentially by rotating the diffraction grating 21, i.e., by sweeping a range of wavelengths.

Figure 2:
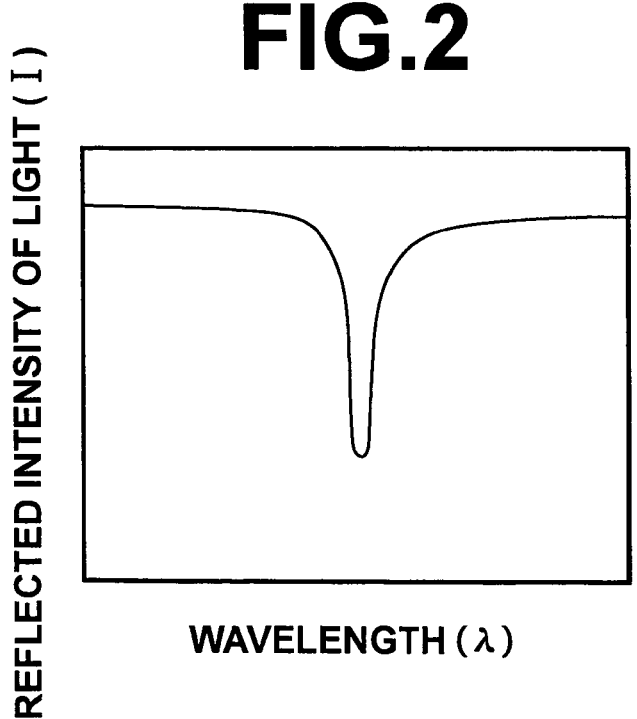
FIG. 2 is a graph illustrating the relationship between the wavelength of a light beam and the reflected intensity of the light beam for a surface plasmon resonance measuring apparatus shown in FIG. 1.

When the white light beam L is totally reflected at the interface 11a, an evanescent wave propagates from the interface 11a to the thin metal film 12 at a predetermined wavelength depending on the refractive index of the interface 11a, and the evanescent wave goes into resonance with the surface plasmons excited on the surface of the thin metal film 12, so that the reflected intensity of the light of the predetermined wavelength drops sharply. FIG. 2 is a graph illustrating the relationship between the wavelength$\lambda$ and the reflected intensity of light when the attenuated total reflection is induced by the surface plasmon resonance. The wavelength for exciting the evanescent wave on the thin metal film 12 differs from place to place on the thin metal film depending on whether or not a particular substance is present there. Accordingly, for example, if the distribution of optical intensities for the light beam L1 having a wavelength $\lambda 1$ that will cause surface plasmon resonance when a particular substance in a sample 13 is present on the thin metal film is imaged, attenuated total reflection will be observed at a place on the thin metal film where the particular substance is present. That is, the two-dimensional distribution of a particular substance in a sample may be observed by making use of attenuated total reflection. More specifically, the data on two-dimensional properties of a particular substance (target substance for analysis) distributed in a sample may be obtained, for example, by conducting measurement with a gel sheet sample used in electrophoretic migration placed on the thin metal film.

Further, in this embodiment, the light beam L1 having a wavelength $\lambda 1$ is selected from the light beam L totally reflected at the interface 11a of the dielectric block 11, and the distribution of optical intensities for the selected light beam L1 is measured, so that stray light may be blocked in the step of selecting the light beam L1 from the light beam L, and the wavelength selection filter employed in the conventional surface plasmon resonance measuring apparatus may be eliminated; thereby reduced size and cost for the measuring apparatus may be realized.

Further, the dielectric prism 11 is shaped in such a manner that the surface 11b of the dielectric prism 11 becomes substantially perpendicular to the light axis of the light beam L entering into the dielectric prism 11, so that the dispersion of the light beam L at the dielectric prism 11 is suppressed, and the accuracy of the measurement may be improved. In addition, the dielectric prism 11 is shaped in such a manner that the surface 11c of the dielectric prism 11 becomes also substantially perpendicular to the light axis of the light beam L totally reflected at the interface 11a and exits from the surface 11c, so that the dispersion at the dielectric prism is further suppressed. Further, no special dispersion suppressing structure is required for suppressing the dispersion of the light beam L at the dielectric prism 11.

Further, the wavelength selection means comprises the diffraction grating 21, converging lens 22, slit 23, and the collimating lens 24, and the light beam L is separated by the diffraction grating 21, the light beam L1 selected by the diffraction grating 21 is converged by the converging lens 22 to pass through the slit 23, and the light beam L1 is collimated by the collimating lens 24, so that a desired wavelength may be readily selected by rotating the diffraction grating 21 with a motor (not shown). This embodiment uses the diffraction grating 21 as the separating means, but the present invention is not limited to the diffraction grating for the separating means; and, for example, a spectroscopic prism or the like may also be used.

Figure 3:
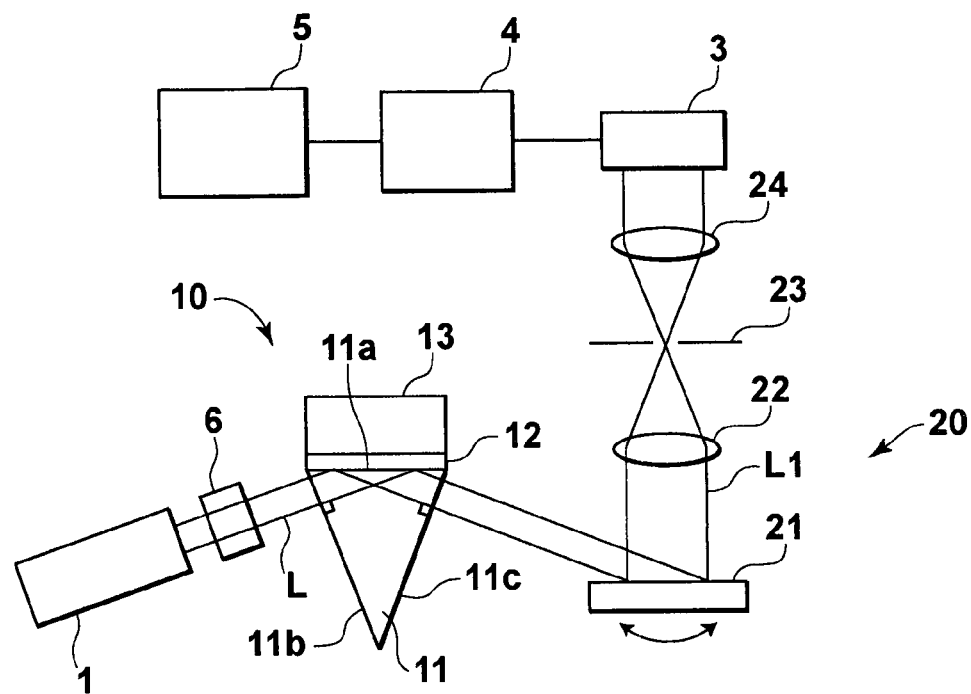
FIG. 3 is a side view of a modified example of a surface plasmon resonance measuring apparatus shown in FIG. 1.

Further, when the dielectric prism 11 is not constructed in such a manner that it is able to suppress the dispersion at the dielectric prism 11 as described above, a dispersion compensating section 6 for compensating for the dispersion at the dielectric prism 11 may be used as shown in FIG. 3. The dispersion compensating section may be placed between the light source 1 and dielectric prism 11, or between the dielectric prism 11 and diffraction grating 21.

Figure 4:
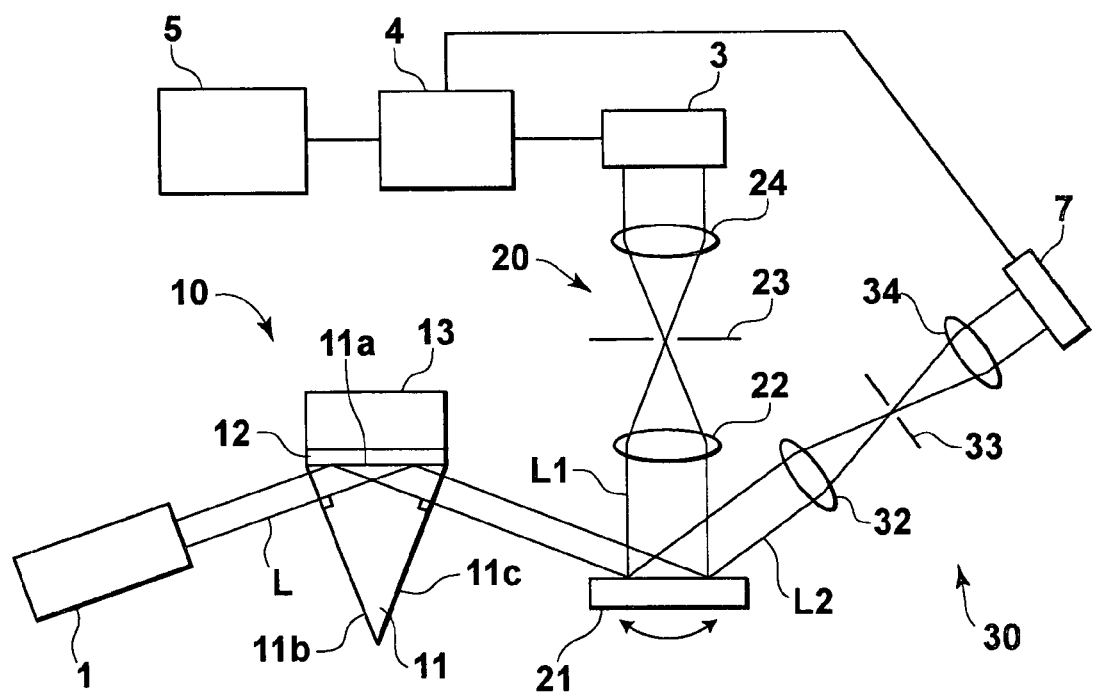
FIG. 4 is a side view of a surface plasmon resonance measuring apparatus according to a second embodiment of the present invention.

Hereinafter, the second embodiment of the present invention will be described with reference to FIG. 4. In FIG. 4, the elements identical to those shown in FIG. 1 are given the same numerical symbols, and will not be elaborated upon further here unless otherwise required.

The measuring apparatus according to the second embodiment of the present invention is also a surface plasmon resonance measuring apparatus, which comprises the measuring apparatus shown in FIG. 1 with an added wavelength selecting section 30 that shares the diffraction grating with the wavelength selecting section 20, and having an identical configuration to that of the wavelength selecting section 20, and a CCD 7 for picking up the image of the distribution of optical intensities for a light beam L2 selected by the wavelength selecting section 30 as a two-dimensional image.

The wavelength selecting section 30 comprises the diffraction grating 21; and three other optical components disposed linearly between the diffraction grating 21 and the CCD 7, namely a converging lens 32, slit 33, and collimating lens 34. The slit 33 is disposed in the vicinity of the focal point of the converging lens 32 to block light other than the light reflected from the diffraction grating 21 to the converging lens 32. This allows that only the light beam reflected to the converging lens 32, i.e., a light beam L2 having a wavelength $\lambda 2$ is to be selected, and the image of the distribution of optical intensities for the selected light beam is picked up by the CCD 7.

In this embodiment, the light beam L1 and Light beam L2 are selected simultaneously, and the distributions of optical intensities for these two light beams may be detected, so that the measuring efficiency may be enhanced. In addition, the comparison between the states of attenuated total reflection for different wavelengths may be readily made.

Figure 5:
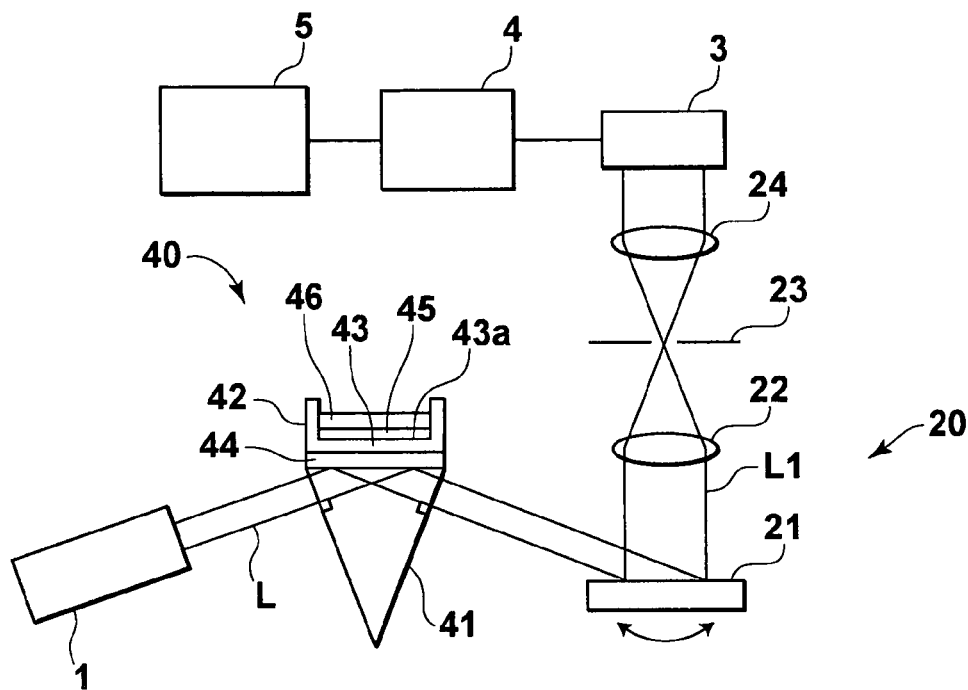
FIG. 5 is a side view of a surface plasmon resonance measuring apparatus according to a third embodiment of the present invention.

Hereinafter, a third embodiment of the present invention will be described with reference to FIG. 5. In FIG. 5, the elements identical to those shown in FIG. 1 are given the same numerical symbols, and will not be elaborated upon further here unless otherwise required.

The measuring apparatus according to the third embodiment of the present invention is also a surface plasmon resonance measuring apparatus having a measuring unit 40 which is different in structure from that shown in FIG. 1. The measuring unit 40 according to this embodiment comprises a dielectric prism 41, and a container section 42 having a liquid reservoir for holding a liquid sample. The bottom section 43 of the container section 42 and the prism 41 have the same refractive index, and connected with each other through a refractive index matching means 44. A thin metal film 45 is provided on the side of liquid reservoir of the bottom section 43 of the container section 42, and a liquid sample 46 is filled on the thin metal film 45. The sample may be replaced readily together with the container section 42 as necessary. The container section 42 serves as a sample holding structure of the present invention.

The collimated light beam L enters from a surface of the prism 41, passes through the prism 41, refractive index matching means 44, and bottom section 43 of the container section 42, and is incident on a predetermined region (a region defined in accordance with the cross sectional area of the light beam) of the interface 43a between the bottom section 43 and thin metal film 45, reflected at the interface 43a, and exits from another surface of the prism 41. Thereafter, a light beam L1 having a wavelength λ1 is selected, and the distribution of optical intensities for this light beam is displayed as a visible image as in the first embodiment. The processes for picking up the image of the distribution of optical intensities for this light beam, and measuring the distribution of refractive indices of the sample 46 based on the picked-up image are identical to those described in the first embodiment. The measuring apparatus according to this embodiment offers enhanced measuring efficiency and reduced measuring cost, as well as those advantages described in the first embodiment, since the container section 42 is readily replaceable for the dielectric prism 41.

Figure 6:
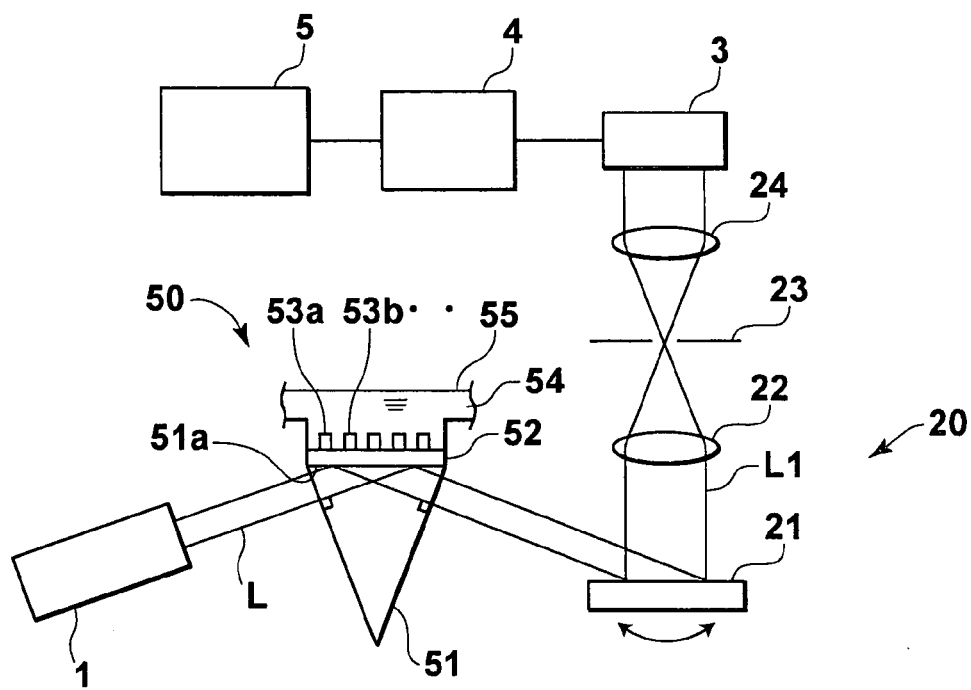
FIG. 6 is a side view of a surface plasmon resonance measuring apparatus according to a fourth embodiment of the present invention.

Hereinafter, a fourth embodiment of the present invention will be described with reference to FIG. 6. The measuring apparatus according to the fourth embodiment of the present invention is also a surface plasmon resonance measuring apparatus having a measuring unit 50 which is different in structure from that shown in FIG. 1. The measuring unit 50 according to this embodiment comprises a dielectric prism 51; a thin metal film 52 made of, for example, gold, silver, copper, aluminum, etc. formed on the upper surface of the dielectric prism 51; a plurality of sensing materials 53a, 53b . . . of different kinds disposed on different places of the thin metal film 52; and a sample holding section 55 having a fluid channel for flowing a liquid sample 54 in and out of the sample holding section 55 while in contact with the sensing materials 53a, 53b . . . .

Respective sensing materials 53a, 53b . . . interact with respective substances of different kinds. One example of the combination of a particular substance and sensing material may be an antigen and antibody. More specifically, the measuring apparatus according to this embodiment may test whether or not a particular substance that reacts to any of the sensing materials 53a, 53b . . . is present in the sample 54 by providing a plurality of sensing materials 53a, 53b . . . of different kinds.

In measuring the liquid sample 54, the concentration of the liquid sample may be changed due to the reaction of a particular substance in the sample with a sensing material. But the change in the concentration of the liquid sample 54 may be prevented by flowing the liquid sample 54 in and out of the sample holding section 55 while in contact with the sensing materials 53a, 53b . . . , as in this embodiment, thereby the concentration of the liquid sample 54 is maintained always constant, allowing measurement for the liquid sample 54 having constant concentration, i.e., measurement under the same measuring conditions.

A collimated light beam L enters into the interface 51a between the prism 51 and thin metal film 52. In this case, the size of the cross sectional area of the light beam L is adapted to illuminate substantially over the range of the thin metal film 52 where the plurality of sensing materials 53a, 53b . . . is disposed. Thereafter, a light beam L1 having a wavelength λ1 is selected from the reflected light beam L reflected at the interface 51a, and the distribution of optical intensities for this light beam is displayed as a visible image as in the first embodiment. By observing the light intensity on the display section 5 corresponding to each of the sensing materials 53a, 53b . . . , existence of a particular substance, or the concentration of the substance and the like may be detected.

Figure 7:
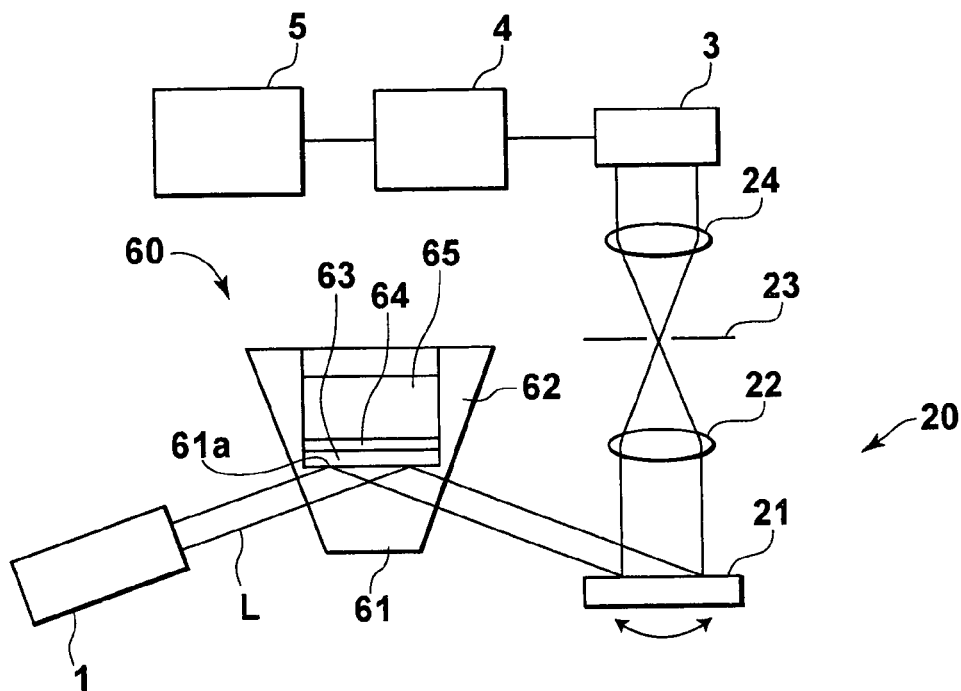
FIG. 7 is a side view of a surface plasmon resonance measuring apparatus according to a fifth embodiment of the present invention.

Hereinafter, a fifth embodiment of the present invention will be described with reference to FIG. 7. The measuring apparatus according to the fifth embodiment of the present invention is also a surface plasmon resonance measuring apparatus having a measuring unit 60 which is different in structure from that shown in FIG. 1. The measuring unit 60 according to this embodiment comprises a dielectric block 61 shaped like a frustum of an inverted quadrangular pyramid having light beam entrance and exit sections, and a container section 62 for holding a liquid sample 65 formed as a single block; and a thin metal film 63 made of, for example, gold, silver, copper, aluminum, etc. formed on the bottom surface of the container section 62 of the dielectric block 61. In addition, the measuring unit 60 has a sensing material 64 fixed on the thin metal film 63.

In this embodiment, a light bema L emitted from a light source 1 enters from a surface of the dielectric block 61, passes through the dielectric block, and is incident on the interface 61a between the dielectric block and thin metal film 63. The light beam L incident on the interface 61a is totally reflected at the interface, and the totally reflected light beam L exits from another surface of the dielectric block 61. Thereafter, a light beam L1 having a wavelength λ1 is selected, and the distribution of optical intensities for this light beam is displayed as a visible image as in the first embodiment. In this configuration, the refractive index of the sensing material 64 varies in accordance with the combined state of a particular substance contained in the sample 65 with the sensing material 64. Thus, the distribution of the refractive indices of the sensing material 64, i.e., the distribution of the combined states of the particular substance contained in the sample with the sensing material 64 may be obtained by picking up the image of the distribution of optical intensities on the cross section of the light beam L1 reflected at the interface by a CCD 3, and making use of the image obtained by the CCD 3.

The measuring unit 60 is formed as a single block having the dielectric block, thin metal film, and sample holding structure, so that the measurement using separate measuring units one after the other may be made by changing the measuring unit 60 in rotation, thereby measuring efficiency is enhanced.

Figure 8:
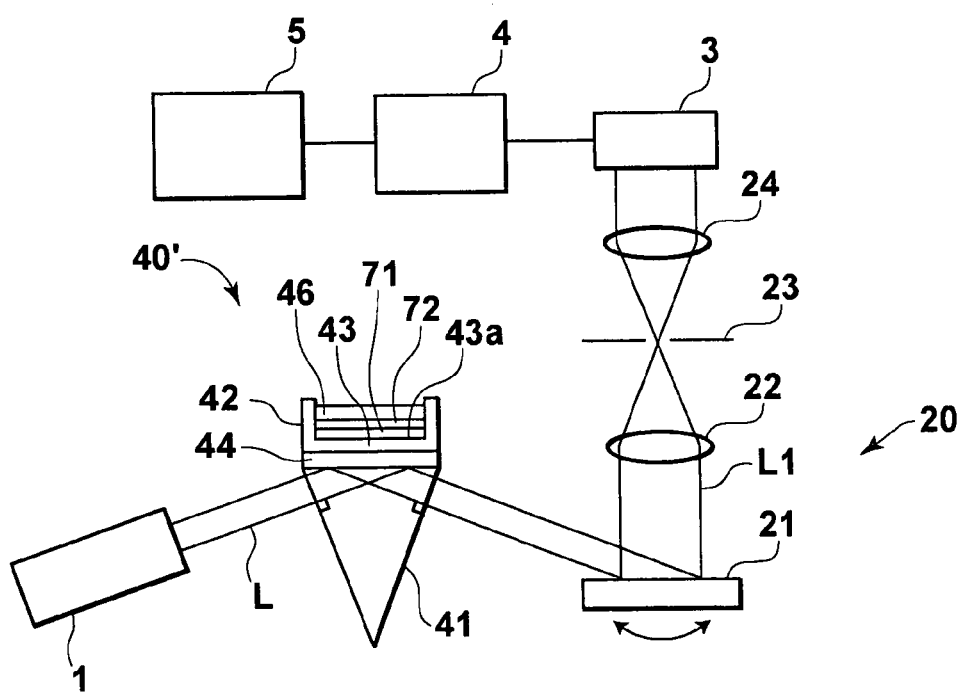
FIG. 8 is a side view of a leaky mode measuring apparatus according to a sixth embodiment of the present invention.

Hereinafter, a sixth embodiment of the present invention will be described with reference to FIG. 8. The measuring apparatus according to the sixth embodiment is a leaky mode measuring apparatus as described earlier. The measuring unit 40' according to this embodiment comprises a dielectric prism 41, and a container section 42 having a liquid reservoir section for holding a liquid sample. A bottom section 43 of the container section 42, and the prism 41 have the same refractive index, and connected with each other through a refractive index matching means 44. A cladding layer 71 is formed on the side of the liquid reservoir of the bottom section 43 of the container section 42, and an optical waveguide layer 72 is formed on the cladding layer 71. A liquid sample 46 is filled on the optical waveguide layer 72. More specifically, the configuration of the measuring apparatus according to this embodiment is similar to that of the measuring apparatus according to the third embodiment described above, except that it has the cladding layer 71 and the optical waveguide layer 72 instead of the thin metal film.

The dielectric prism 41 according to this embodiment is formed, for example, with a synthetic resin, or an optical glass such as BK7. The cladding layer 71 is formed in a thin film using a dielectric material, or a metal such as gold having smaller refractive index than that of the dielectric prism 41. The optical waveguide layer 72 is formed also in a thin film using a dielectric material having a greater refractive index than that of the cladding layer 71, such as PMMA. The thickness of the cladding layer is about 36.5 nm when formed, for example, with a thin gold film, and the thickness of the optical waveguide layer is about 700 nm when formed, for example, with PMMA.

In a leaky mode measuring apparatus configured in the aforementioned manner, when a light beam L emitted from a light source 1 passes through the dielectric prism 41, refractive index matching means 44, the bottom section 43 of the container section 42, and is incident on a predetermined area of the interface between the bottom section 43 of the container section 42 and the cladding layer 71 at a predetermined incident angle not smaller than the total reflection angle, the light beam L is totally reflected at the interface 41a, but a light component having a certain wave number that has passed through the cladding layer 71 and enters into the optical waveguide layer 72 at a certain incident angle propagates along the optical waveguide layer in a waveguide mode. When the waveguide mode is excited in this manner, attenuated total reflection occurs, in which the intensity of the light totally reflected at the interface 43 drops sharply, because most of the incident light is contained in the optical waveguide layer 72.

The wave number of the guided light propagating along the optical waveguide layer 72 is dependent on the refractive index of the sample 46 placed on the optical waveguide layer 72. Thus, in this case also, the distribution of the refractive indices of the sample 46 may be measured by using the attenuated total reflection, if a light beam L1 having a predetermined wavelength λ1 is selected from the light beam L reflected at the interface, and the image of the distribution of optical intensities on the cross section of the light beam L1 is picked up by a CCD 5 to reproduce it as a visual image.

In this case, the light beam L1 having a predetermined wavelength λ1 is selected from the light beam L totally reflected at the interface 41a, and the distribution of optical intensities for the light beam L1 is measured, so that stray light may be blocked in the step of selecting the light beam L1 from the light beam L, and the wavelength selection filter employed in the conventional leaky mode measuring apparatus may be eliminated, thereby reduced size and cost for the measuring apparatus may be realized.

In the third to sixth embodiments, a measuring apparatus having a single wavelength selecting section is described. But the measuring apparatus according to the present invention may have two wavelength selecting sections as in the second embodiment, or it may have three or more wavelength selecting sections. Further, the measuring apparatus according to the present invention may have a wavelength selecting section that sequentially sweeps a range of wavelengths by rotating a diffraction grating to measure the distributions of optical intensities continuously, instead of using a wavelength selecting section that selects a light beam of a predefined wavelength from the light beam L. Still further, in each of the preferred embodiments, a selecting means having a diffraction grating is used as the selecting section, but the present invention is not limited to these embodiments. It may be anything as long as it has a wavelength selection capability, such as a prism. The use of a cooled CCD as the CCD will result in a further enhanced accuracy of measurement. A photodetector comprising photodiodes may also be used instead of the CCD, in which case faster measurement and further accurate measurement results may be obtained.

What is claimed is:

1. A measuring method using attenuated total reflection comprising the steps of:

entering a collimated light beam containing a plurality of wavelengths, and having a sizable cross sectional area, through a dielectric block of a measuring unit comprising a thin film layer formed on one of the surfaces of said dielectric block, and a sample holding structure for holding a sample provided on said thin film layer, into the interface between said dielectric block and said thin film layer at an angle that satisfies the conditions of attenuated total reflection at said interface;

selecting a collimated light beam having a predetermined wavelength from the collimated light beam totally reflected from said interface; and measuring the distribution of optical intensities on the cross section of said selected light beam, wherein said selecting step comprises a variable selection of said predetermined wavelength of said collimated light beam.

2. A measuring method according to claim 1, wherein said wavelength selecting step selects a plurality of collimated light beams of different wavelengths simultaneously; and said measuring step detects the respective distributions of optical intensities on the cross sections of said plurality of collimated light beams of different wavelength.

3. A measuring method according to claim 1, wherein said wavelength selecting step separates said collimated light beam into spectral components, converges a part of said spectral components to pass through a slit and thereafter transforms said converged spectral components into a collimated light beam, and wherein a relative angle between said separated collimated light beam and said converged spectral components is changeable.

4. A measuring apparatus using attenuated total reflection comprising:

a measuring unit comprising a thin film layer formed on one of the surfaces of a dielectric block, and a sample holding structure for holding a sample provided on said thin film layer;

an illuminating means for entering a collimated light beam containing a plurality of wavelengths, and having a sizable cross sectional area, which is generated, and emitted from a light source, into the interface between said dielectric block, and said thin film layer, through said dielectric block, at an angle that satisfies the conditions of total reflection at said interface;

a wavelength selecting means disposed in the optical path of the collimated light beam totally reflected from said interface, and adapted to select a collimated light beam having a predetermined wavelength from said collimated light beam containing said plurality of wavelengths; and a two-dimensional optical detecting means for detecting the distribution of optical intensities on the cross section of said collimated light beam selected by said wavelength selecting means, wherein said wavelength selecting means variably selects said predetermined wavelength of said collimated light beam.

5. A measuring apparatus according to claim 4, wherein said wavelength selecting means further comprises:
a separating means separating said collimated light beam into spectral components;
a selecting means converging a part of said spectral components to pass through a slit and transforming said converged spectral components into a collimated light beam; and
a sweeping means changing the relative angle between said separating means and said selecting means;
wherein said wavelength selecting means is adapted to select a plurality of collimated light beams of different wavelength simultaneously.

6. A measuring apparatus according to claim 4, wherein said wavelength selecting means is adapted to select a plurality of collimated light beams of different wavelength simultaneously; and said two-dimensional optical detecting means is adapted to detect the respective distributions of optical intensities on the cross sections of said plurality of collimated light beams of different wavelength.

7. A measuring apparatus according to claim 4, wherein said apparatus further comprises a dispersion suppressing structure for suppressing the dispersion of said collimated light beam at said dielectric block.

8. A measuring apparatus according to claim 4, wherein said apparatus further comprises a dispersion compensating means for compensating for the dispersion of said collimated light beam at said dielectric block.

9. A measuring apparatus according to claim 4, wherein said thin film layer has a sensing material thereon that interacts with a specific component of said sample.

10. A measuring apparatus according to claim 4, wherein said wavelength selecting means comprises a separating means for separating said collimated light beam into spectral components; a selecting means for converging a part of said spectral components to pass through a slit, and thereafter transforming said converged spectral component into a collimated light beam; and a sweeping means for changing the relative angle between said separating means and said selecting means.

11. A measuring apparatus according to claim 6, wherein said apparatus further comprises a dispersion suppressing structure for suppressing the dispersion of said collimated light beam at said dielectric block.

12. A measuring apparatus according to claim 6, wherein said apparatus further comprises a dispersion compensating means for compensating for the dispersion of said collimated light beam at said dielectric block.

13. A measuring apparatus according to claim 6, wherein said thin film layer has a sensing material thereon that interacts with a specific component of said sample.

14. A measuring apparatus according to claim 6, wherein said wavelength selecting means comprises a separating means for separating said collimated light beam into spectral components; a selecting means for converging a part of said spectral components to pass through a slit, and thereafter transforming said converged spectral component into a collimated light beam; and a sweeping means for changing the relative angle between said separating means and said selecting means.

15. A measuring apparatus according to claim 7, wherein said dielectric block is formed such that the optical entrance surface thereof is perpendicular to the optical axis of said collimated light beam, and serves as said dispersion suppressing structure.

16. A measuring apparatus according to claim 7, wherein said thin film layer has a sensing material thereon that interacts with a specific component of said sample.

17. A measuring apparatus according to claim 7, wherein said wavelength selecting means comprises a separating means for separating said collimated light beam into spectral components; a selecting means for converging a part of said spectral components to pass through a slit, and thereafter transforming said converged spectral component into a collimated light beam; and a sweeping means for changing the relative angle between said separating means and said selecting means.

18. A measuring apparatus according to claim 11, wherein said dielectric block is formed such that the optical entrance surface thereof is perpendicular to the optical axis of said collimated light beam, and serves as said dispersion suppressing structure.

19. A measuring apparatus according to claim 11, wherein said thin film layer has a sensing material thereon that interacts with a specific component of said sample.

20. A measuring apparatus according to claim 11, wherein said wavelength selecting means comprises a separating means for separating said collimated light beam into spectral components; a selecting means for converging a part of said spectral components to pass through a slit, and thereafter transforming said converged spectral component into a collimated light beam; and a sweeping means for changing the relative angle between said separating means and said selecting means.

21. A measuring apparatus according to claim 8, wherein said thin film layer has a sensing material thereon that interacts with a specific component of said sample.

22. A measuring apparatus according to claim 8, wherein said wavelength selecting means comprises a separating means for separating said collimated light beam into spectral components; a selecting means for converging a part of said spectral components to pass through a slit, and thereafter transforming said converged spectral component into a collimated light beam; and a sweeping means for changing the relative angle between said separating means and said selecting means.

23. A measuring apparatus according to claim 12, wherein said thin film layer has a sensing material thereon that interacts with a specific component of said sample.

24. A measuring apparatus according to claim 12, wherein said wavelength selecting means comprises a separating means for separating said collimated light beam into spectral components; a selecting means for converging a part of said spectral components to pass through a slit, and thereafter transforming said converged spectral component into a collimated light beam; and a sweeping means for changing the relative angle between said separating means and said selecting means.

25. A measuring apparatus according to claim 9, wherein said wavelength selecting means comprises a separating means for separating said collimated light beam into spectral components; a selecting means for converging a part of said spectral components to pass through a slit, and thereafter transforming said converged spectral component into a collimated light beam; and a sweeping means for changing the relative angle between said separating means and said selecting means.

26. A measuring apparatus according to claim 13, wherein said wavelength selecting means comprises a separating means for separating said collimated light beam into spectral components; a selecting means for converging a part of said spectral components to pass through a slit, and thereafter transforming said converged spectral component into a collimated light beam; and a sweeping means for changing the relative angle between said separating means and said selecting means.

27. A measuring apparatus according to claim 16, wherein said wavelength selecting means comprises a separating means for separating said collimated light beam into spectral components; a selecting means for converging a part of said spectral components to pass through a slit, and thereafter transforming said converged spectral component into a collimated light beam; and a sweeping means for changing the relative angle between said separating means and said selecting means.

28. A measuring apparatus according to claim 19, wherein said wavelength selecting means comprises a separating means for separating said collimated light beam into spectral components; a selecting means for converging a part of said spectral components to pass through a slit, and thereafter transforming said converged spectral component into a collimated light beam; and a sweeping means for changing the relative angle between said separating means and said selecting means.

29. A measuring apparatus according to claim 21, wherein said wavelength selecting means comprises a separating means for separating said collimated light beam into spectral components; a selecting means for converging a part of said spectral components to pass through a slit, and thereafter transforming said converged spectral component into a collimated light beam; and a sweeping means for changing the relative angle between said separating means and said selecting means.

30. A measuring apparatus according to claim 23, wherein said wavelength selecting means comprises a separating means for separating said collimated light beam into spectral components; a selecting means for converging a part of said spectral components to pass through a slit, and thereafter transforming said converged spectral component into a collimated light beam; and a sweeping means for changing the relative angle between said separating means and said selecting means.

31. A measuring apparatus according to claim 10, wherein said separating means is a diffraction grating, or prism.

32. A measuring apparatus according to claim 14, wherein said separating means is a diffraction grating, or prism.

33. A measuring apparatus according to claim 17, wherein said separating means is a diffraction grating, or prism.

34. A measuring apparatus according to claim 20, wherein said separating means is a diffraction grating, or prism.

35. A measuring apparatus according to claim 22, wherein said separating means is a diffraction grating, or prism.

36. A measuring apparatus according to claim 24, wherein said separating means is a diffraction grating, or prism.

37. A measuring apparatus using attenuated total reflection comprising:
a measuring unit comprising a thin film layer formed on one of the surfaces of a dielectric block, and a sample holding structure for holding a sample provided on said thin film layer;
an illuminating means for entering a collimated light beam containing a plurality of wavelengths, and having a sizable cross sectional area, which is generated, and emitted from a light source, into the interface between said dielectric block, and said thin film layer, through said dielectric block, at an angle that satisfies the conditions of total reflection at said interface;
a wavelength selecting means disposed in the optical path of the collimated light beam totally reflected from said interface, and adapted to select a collimated light beam having a predetermined wavelength from said collimated light beam containing said plurality of wavelengths; and
a two-dimensional optical detecting means for detecting the distribution of optical intensities on the cross section of said collimated light beam selected by said wavelength selecting means,
wherein said wavelength selecting means comprises:
a separating means;
a selecting means; and
a sweeping means;
wherein said sweeping means changes the relative angle of a light beam output from said separating means to said selecting means, and said wavelength selecting means is adapted to select a plurality of collimated light beams of different wavelength simultaneously.

38. A measuring apparatus using attenuated total reflection comprising:
a measuring unit comprising a thin film layer formed on one of the surfaces of a dielectric block, and a sample holding structure for holding a sample provided on said thin film layer;
an illuminating means for entering a collimated light beam containing a plurality of wavelengths, and having a sizable cross sectional area, which is generated, and emitted from a light source, into the interface between said dielectric block, and said thin film layer, through said dielectric block, at an angle that satisfies the conditions of total reflection at said interface;
a wavelength selecting means disposed in the optical path of the collimated light beam totally reflected from said interface, and adapted to select a collimated light beam having a predetermined wavelength from said collimated light beam containing said plurality of wavelengths; and
a two-dimensional optical detecting means for detecting the distribution of optical intensities on the cross section of said collimated light beam selected by said wavelength selecting means,
wherein said wavelength selecting means comprises:
a rotatable diffraction grating; and
a slit;
wherein said rotatable diffraction grating separates said collimated light beam into spectral components, and a part of said spectral components is converged to pass through said slit.

39. A measuring apparatus using attenuated total reflection comprising:
a measuring unit comprising a thin film layer formed on one of the surfaces of a dielectric block, and a sample holding structure for holding a sample provided on said thin film layer;
an illuminating means for entering a collimated light beam containing a plurality of wavelengths, and having a sizable cross sectional area, which is generated, and emitted from a light source, into the interface between said dielectric block, and said thin film layer, through said dielectric block, at an angle that satisfies the conditions of total reflection at said interface;
a wavelength selecting means disposed in the optical path of the collimated light beam totally reflected from said interface, and adapted to select a collimated light beam having a predetermined wavelength from said collimated light beam containing said plurality of wavelengths; and a two-dimensional optical detecting means for detecting the distribution of optical intensities on the cross section of said collimated light beam selected by said wavelength selecting means, wherein said wavelength selecting means comprises a separating means for separating said collimated light beam into spectral components; a selecting means for converging a part of said spectral components to pass through a slit, and thereafter transforming said converged spectral components into a collimated light beam; and a sweeping means for changing the relative angle between said separating means and said selecting means.

* * * * *